(12) United States Patent
Ritola (10) Patent No.: US 8,402,887 B2
(45) Date of Patent: Mar. 26, 2013

(54) CLAMP

(76) Inventor: Irvin W. Ritola, Vancouver, WA (US)

( * ) Notice: Subject to any disclaimer, the term of this patent is extended or adjusted under 35 U.S.C. 154(b) by 343 days.

(21) Appl. No.: 12/622,091

(22) Filed: Nov. 19, 2009

(65) Prior Publication Data

US 2010/0125981 A1 May 27, 2010

Related U.S. Application Data

(60) Provisional application No. 61/117,825, filed on Nov. 25, 2008.

(51) Int. Cl.
*B65B 13/02* (2006.01)
(52) U.S. Cl. .............................................. 100/2; 100/30
(58) Field of Classification Search .................. 100/2, 8, 100/9, 29, 30, 32, 33 PB, 212; 24/265 EC, 24/265 R
See application file for complete search history.

(56) References Cited

U.S. PATENT DOCUMENTS

| | | | | |
|---|---|---|---|---|
| 4,714,016 A | * | 12/1987 | Bond | 100/212 |
| 5,572,771 A | * | 11/1996 | Kelleghan | 24/170 |
| 7,290,486 B2 | * | 11/2007 | Lafond | 100/295 |
| 7,591,222 B2 | * | 9/2009 | Alain | 100/295 |

* cited by examiner

*Primary Examiner* — Jimmy T Nguyen
(74) *Attorney, Agent, or Firm* — Stoel Rives LLP (57) ABSTRACT

A lever for binding items with a strap may not be attached to the item and function to tension a strap around the item. The strap may engage the lever by bending an end of the strap to secure the strap through a plurality of apertures in the lever, by friction, by pressure, by any combination of the foregoing, or other suitable manner. A lever may lock in a closed position using a locking device, such as an over-center mechanism, a retaining clip, or a strap engaging portion.

11 Claims, 15 Drawing Sheets

SHAPED ASSY WITH
CURVED BINDER AND
STEEL STRAPS

DETAIL 'A'
CURVED BINDER
AND STEEL STRAPS

FIGURE 4B END VIEW

**FIGURE 16
SHOWN WITH STEEL BANDING**

SOFT SURFACE
SELF-HOLDING BINDER
FIGURE 17A

HARD SURFACE
SELF-HOLDING BINDER
FIGURE 17B

FIGURE 17C

HARD SURFACE
SELF-HOLDING BINDER
WITH POLY STRAPS

FIGURE 23
POLY STRAP ISO VIEW

FIGURE 24

FIGURE 25
FLAT BINDER 1 WITH STEEL STRAPS

FIGURE 26

FIGURE 27
SHAPED ASSY WITH CURVED BINDER AND STEEL STRAPS

DETAIL 'A' FIGURE 28
CURVED BINDER AND STEEL STRAPS

CLAMP

RELATED APPLICATIONS

This application claims priority under 35 U.S.C. §119 (e) to U.S. Provisional Patent Application No. 61/117,825, filed Nov. 25, 2008, which is fully incorporated herein by reference.

BACKGROUND

The field of the present invention relates to binders used with straps and methods for using binders with straps.

Straps, such as steel banding or poly straps, are commonly used to bind items to objects, such as a lid to a crate for shipping, a water heater to a wall, goods to a pallet, and various other applications. There are various tools used to tension straps around items, for example, tensioning brackets tensioned by screws turned by a screwdriver or wrench, ratchet assemblies, and crimping tools that crimp a clip in place after another tool has been used to apply tension to the strap.

The present inventor has recognized that using the various, commonly available tools to tension straps is expensive, bulky, and may be cumbersome. The present inventor therefore recognized a need for an improved device for tensioning straps.

SUMMARY

The present invention is directed to devices and methods for binding items with straps. In a preferred configuration, a device for binding items with a strap is a lever that is not attached to an item to be bound and is not attached to any other object. The lever includes an axis of rotation that is proximate to an axis end of the lever, and includes a strap retaining feature. The strap retaining feature is used to secure a first free end of a strap proximate, that is, near, the axis end of the lever. The strap retaining feature is also used to secure a second free end of a strap in a position where the second free end of a strap engages the lever at a point that is distal from the axis end of the lever. The lever also includes a locking device that is configured to maintain tension on a strap and to lock the lever in a closed position when the first free end of a strap and the second free end of a strap are secured to the lever and the lever is rotated from an open position to a closed position.

In a preferred method for securing an item to an object with a strap, the strap is engaged with the object, then placed around the item. A first free end of the strap is secured to a lever so that the first free end engages proximate to an end of the lever. The lever may contact the item and/or the object, but is not attached to either. A second free end of the strap is secured to the lever so that the second free end engages the lever distal from where the first free end engages the lever. The lever is rotated from an open position to a closed position to tension the strap, and is locked in the closed position.

Additional aspects and advantages will be apparent from the following detailed description of preferred embodiments, which proceeds with reference to the accompanying drawings.

BRIEF DESCRIPTION OF THE DRAWINGS

FIG. 15B is a top left isometric view of the lever of FIG. 15A in a closed position.

FIG. 20A is a top left isometric view of a cam device.

FIG. 20B is a top left isometric view of another cam device.

FIG. 20C is a top left isometric view of another lever for binding items.

FIG. 20D is a top left isometric view of the lever of FIG. 20C assembled with the cam device of FIG. 20A.

FIG. 20E is a top left isometric view of the assembly of FIG. 20D with straps attached.

DETAILED DESCRIPTION OF PREFERRED EMBODIMENTS

Preferred embodiments will now be described with reference to the drawings. The preferred embodiments will be described in terms of a lever that is not attached to an item to be secured or bound, and is not attached to another object. But, alternate configurations may be employed with levers of different construction. Preferred embodiments may overcome the above noted problems associated with using current tools to tension straps, or may have other advantages.

Figures 1A, 1B, 1C, 1D, 2A, 2B:
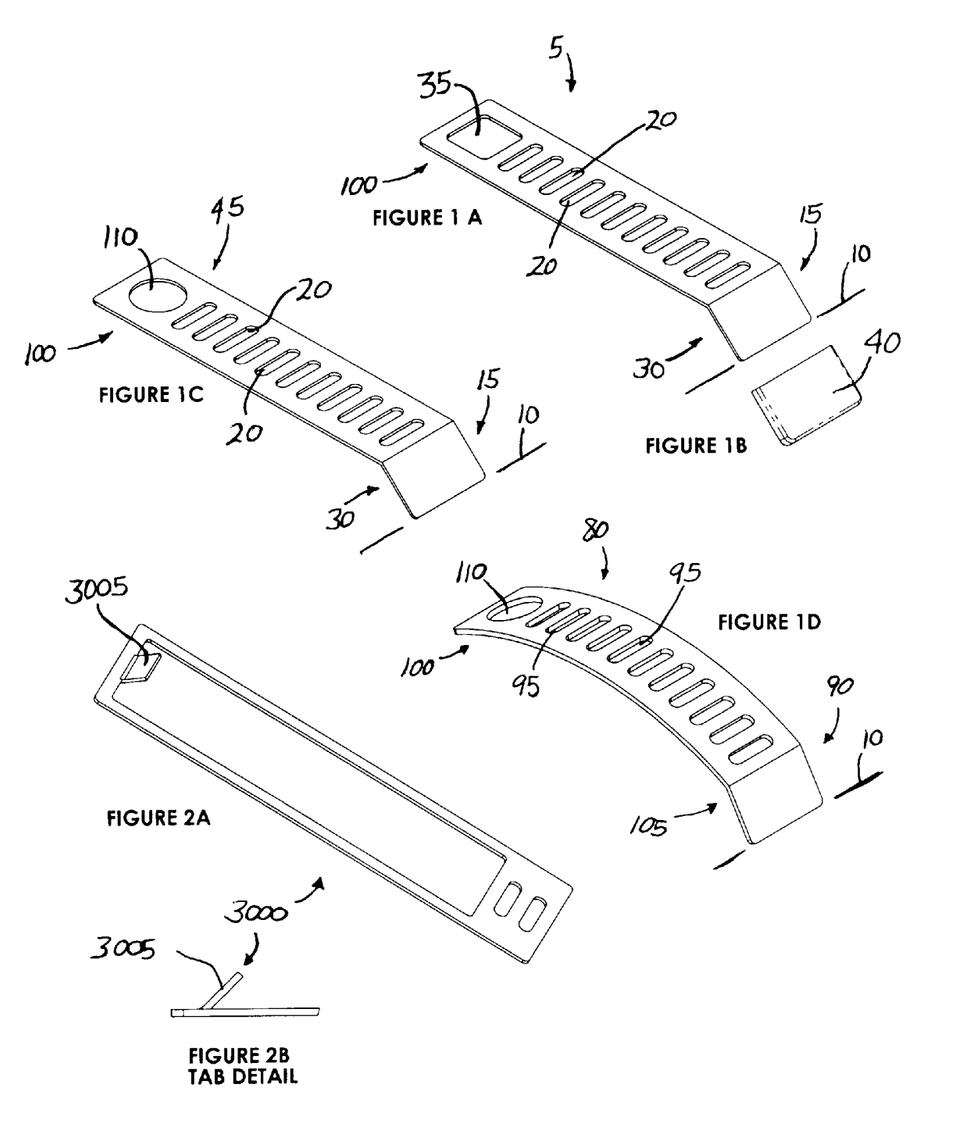
FIG. 1A is a top left isometric view of a lever for binding items.
FIG. 1B is a top left isometric view of a protective boot.
FIG. 1C is a top left isometric view of another lever for binding items.
FIG. 1D is a top left isometric view of another lever for binding items.
FIG. 2A is a top left isometric view of an embodiment of an extension piece.
FIG. 2B is an end view of the extension piece of FIG. 2A.
Figures 27, 28:
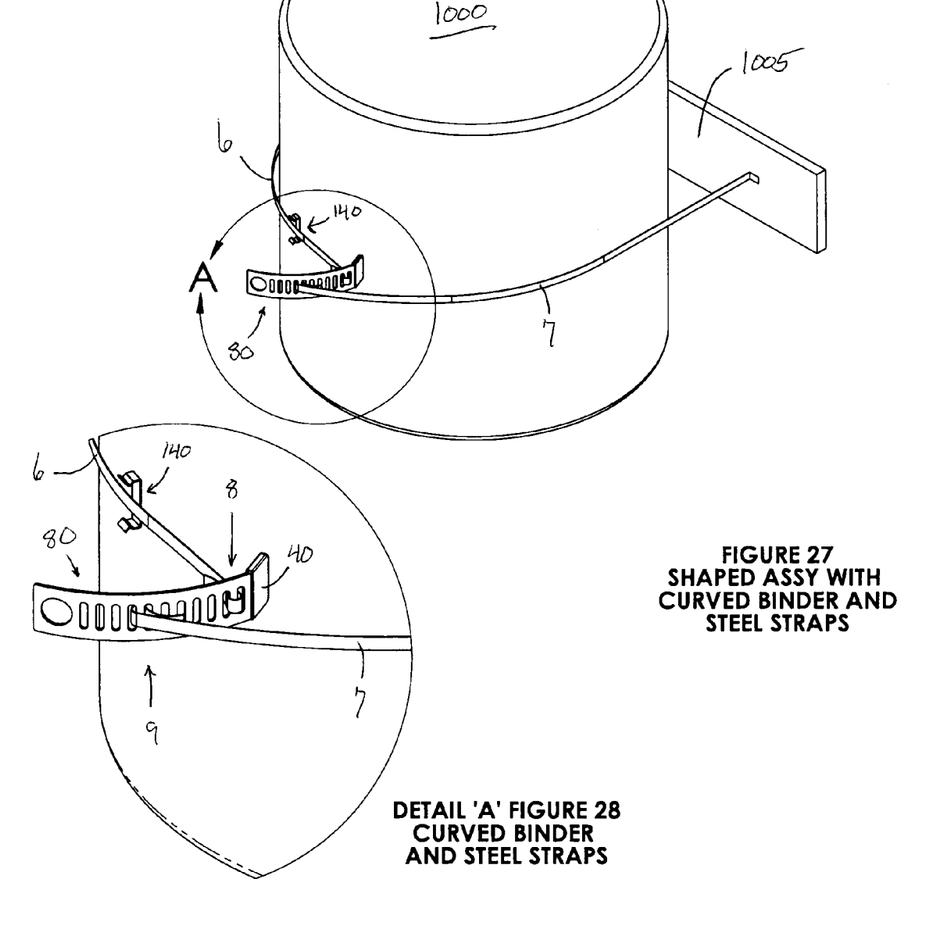
FIG. 27 is a top left isometric view of a lever used to bind an item with straps.
FIG. 28 is a detailed view of the lever of FIG. 27.

Referring to FIGS. 1D, 27, and 28, using a preferred embodiment of a lever 80 (FIG. 1D) to bind an item 1000 to an object 1005 is illustrated. Generally, an object is something that an item is bound to. The lever 80 may be shaped to conform to the surface of the item 1000. A strap 6, 7 is engaged with the object 1005. Engaging a strap to an object may involve attaching or suitably securing the strap to the object, passing a strap through the object, or passing the strap around the object. For example, the object 1005 may be a wall and an end of the strap 6 and an end of the strap 7 may be attached to the wall. Alternately, the strap 6, 7 may be a single strap and may pass through holes in the wall, or otherwise be placed around the object 1005. The strap 6, 7 is preferably passed around the item 1000 for binding the item 1000 to the object 1005.

A first free end 8 of strap 6 may be retained in apertures 95 (FIG. 1D) so that the first free end 8 is proximate the axis end 90 (FIG. 1D). A second free end 9 of strap 7 may be retained in apertures 95 so that the second free end 9 engages the lever 80 distal from the axis end 90. In accordance with the teachings set forth herein, other suitable arrangements for securing a free end of a strap to a lever may be used.

Figure 5A:
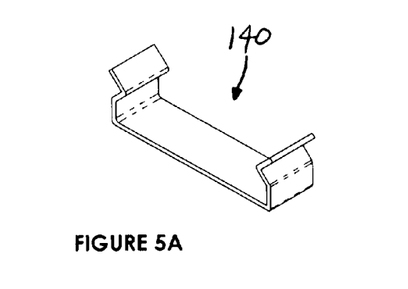
FIG. 5A is a top left isometric view of a retaining clip.

Once the first free end 8 and the second free end 9 are secured to the lever 80, the lever 80 is rotated from an open position (depicted) to a closed position, for example where both the axis end 90 and the distal end 100 of the lever 80 contact (but are not attached to) the item 1000. The lever 80 may be locked in place by the locking device 105. For example, when the distal end 100 of the lever 80 contacts the item 1000, the bent portion of the lever resulting from including the locking device 105 may act as an over-center device to lock the lever 80 in the closed position. Alternatively, or in addition to the locking device 105, a retaining clip 140 (FIG. 5A) may be located so that it is between the item 1000 and the strap 6. When the lever 80 is rotated to the closed position, the lever 80 engages the retaining clip 140, and due to the strap 6 between the retaining clip 140 and the lever 80, the retaining clip 140 locks the lever 80 in the closed position.

FIG. 1A illustrates another preferred embodiment for a lever for binding items using straps. The lever 5 has an axis end 15, and is preferably made from a rigid material such as steel, high strength plastic, or other suitable material. The lever 5 rotates about the rotational axis 10, which is proximate to the axis end 15 of the lever 5. In certain embodiments, the rotational axis 10 may be parallel to and tangent to the axis end 15 of the lever 5. The lever 5 is preferably a free standing device, in other words, the lever 5 is preferably not attached to an item that is to be bound or secured by straps, and the lever 5 is preferably not attached to an object that an item is being bound or secured to.

Figure 23:
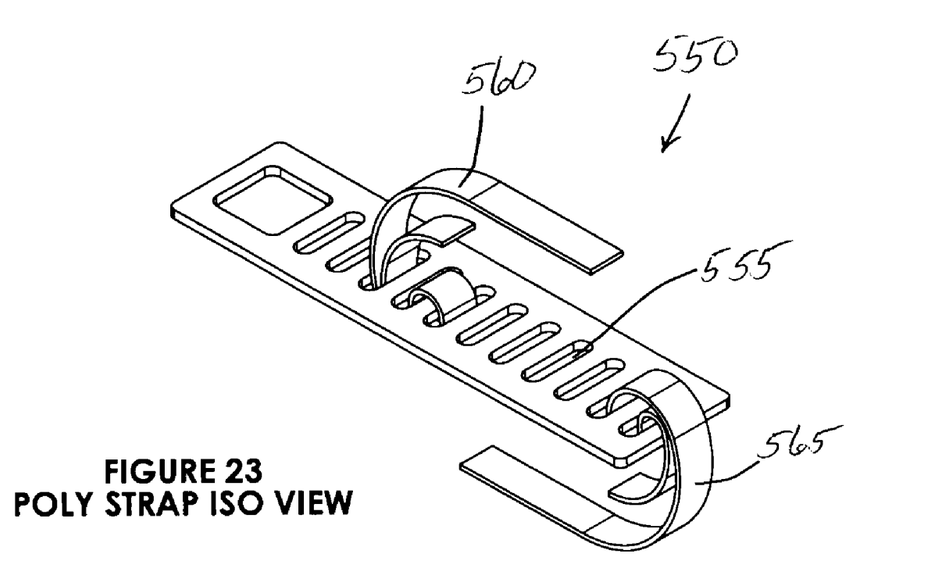
FIG. 23 is a top left isometric view of another lever for binding items with straps retained to the lever.
Figure 24:
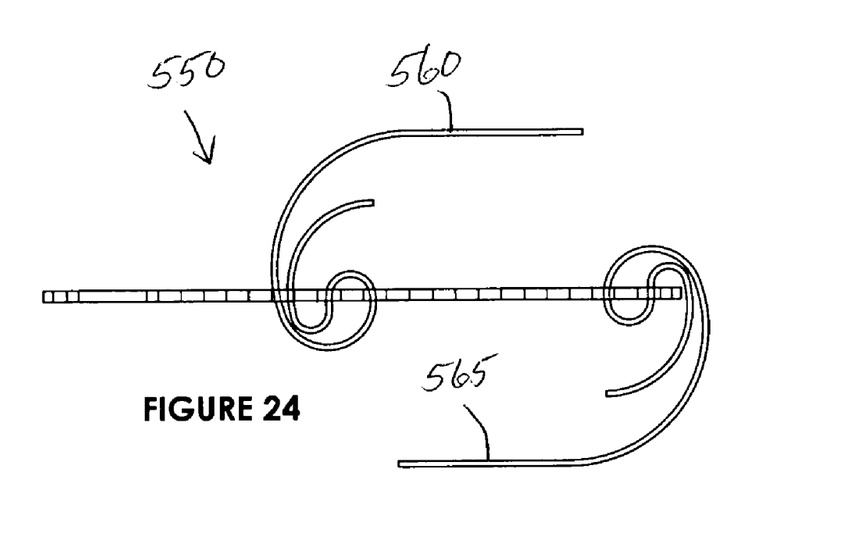
FIG. 24 is a side view of the lever of FIG. 23.
Figure 25:
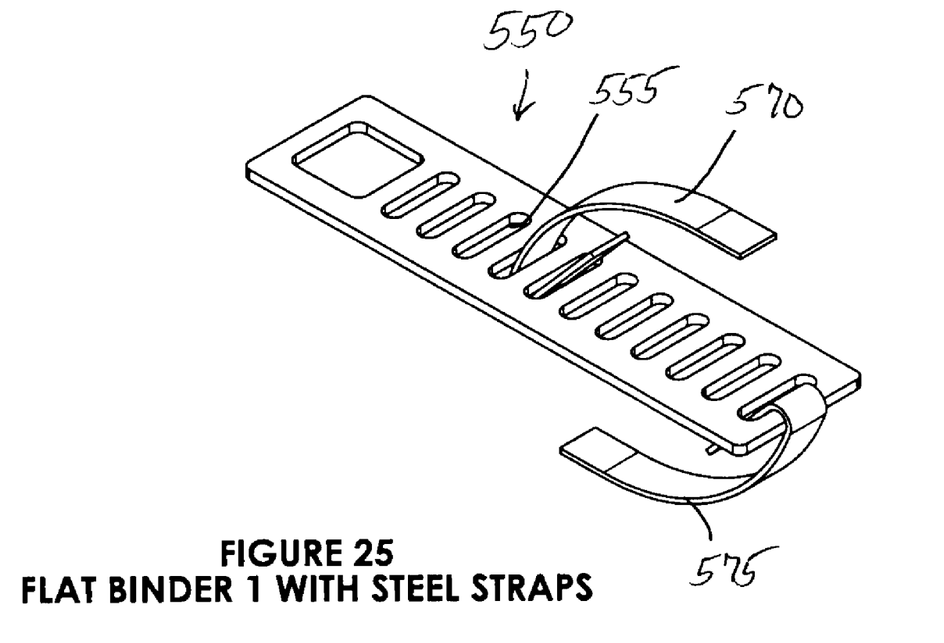
FIG. 25 is a top left isometric view of the lever of FIG. 23 with other straps retained to the lever.
Figure 26:
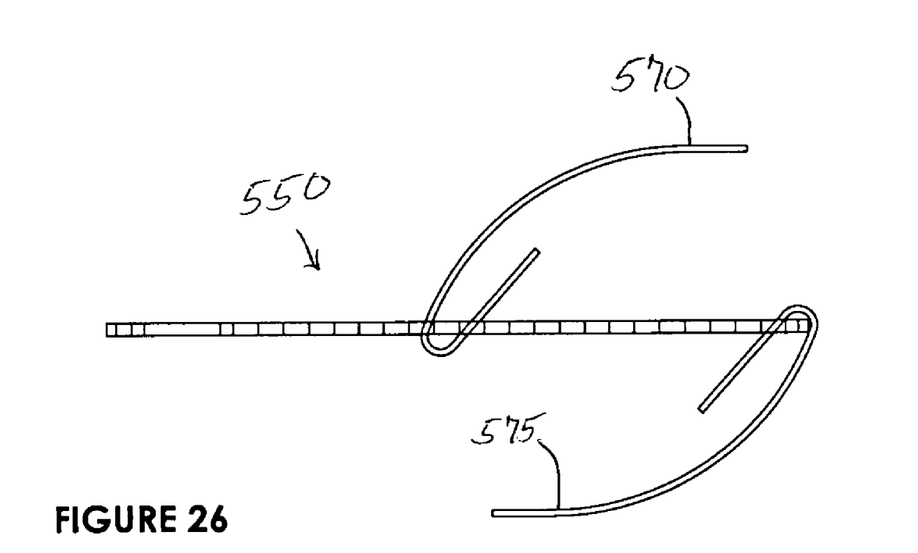
FIG. 26 is a side view of the lever of FIG. 25.

A preferred arrangement for a strap retaining feature is to include a plurality of apertures 20 spaced along the length of the lever 5. As illustrated in FIGS. 23-26, apertures 555 may be used to frictionally secure a first free end of a strap 560 and a second free end of a strap 565 to a lever 550. The first free end and the second free end may be ends of one strap, or may be ends of different straps. FIGS. 23 and 24 illustrate one manner for securing a strap in the plurality of apertures 555. For example, the straps 560 and 565 may be poly straps, for example, straps made from polypropylene, polyester, nylon straps, or other straps, that are relatively smooth, may readily slide over another material, or may not readily deform. FIGS. 25 and 26 illustrate an alternative manner for securing a strap in the plurality of apertures 555. For example, the straps 570 and 575 may be straps made from metal, or other suitable materials, that do not readily slide over another material, or may readily deform. When a readily deformable strap is used, such as steel banding, an end of the strap may be bent to readily fit into an aperture 555 and use the "hook" formed by the bend to assist holding the strap in place.

Figure 3A:
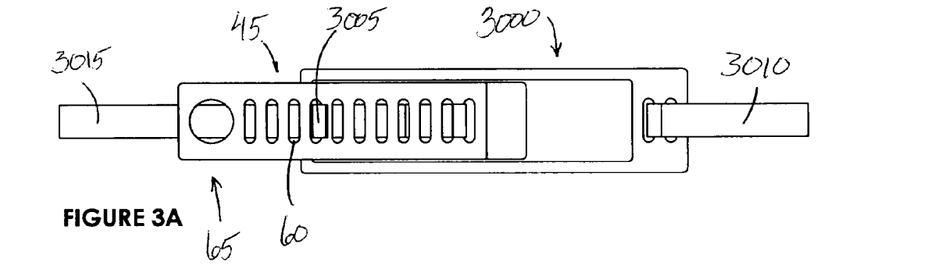
FIG. 3A is a top view of the lever of FIG. 10 used with the extension piece of FIG. 2A.
Figure 3B:
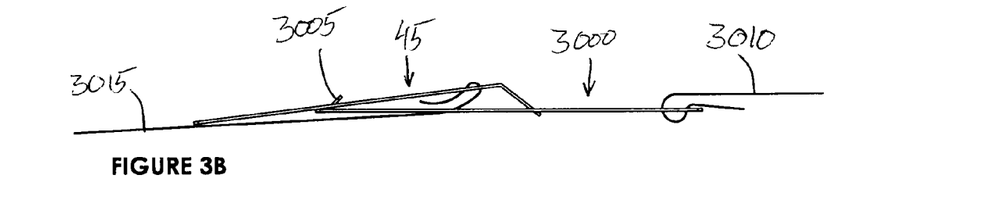
FIG. 3B is a side view of the lever of FIG. 10 used with the extension piece of FIG. 2A.
Figure 3C:
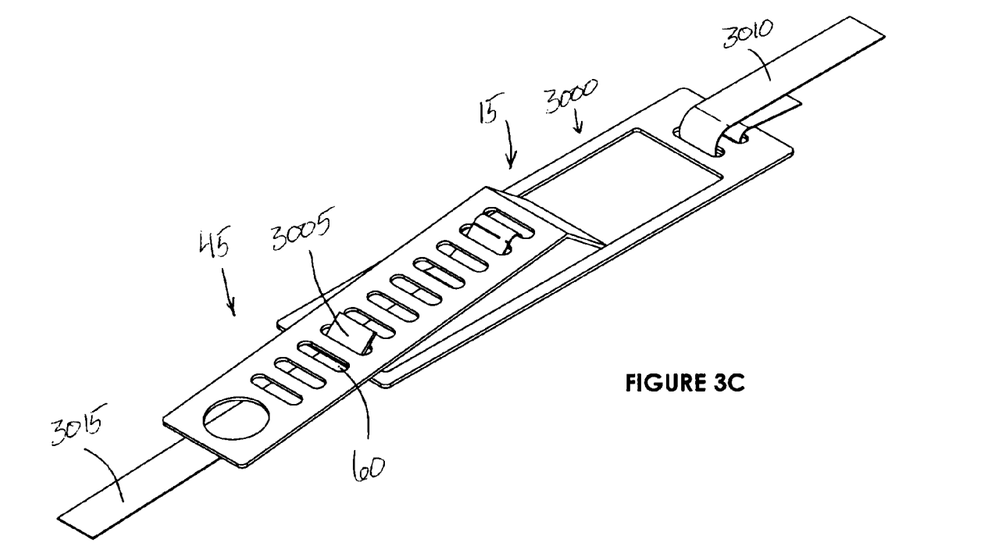
FIG. 3C is a top left isometric of the lever of FIG. 1C used with the extension piece of FIG. 2A.

An alternate to securing straps directly to a lever (such as lever 45 for example) is to secure a strap 3010 to an extension piece 3000 and to secure the extension piece 3000 to a lever, such as lever 45 for example, using a tab 3005, or other suitable structure for releasably securing the extension piece 3000 to a lever. Using an extension piece 3000 may permit a user to repeatedly bind and unbind items of a similar, but slightly variable, size without requiring a user to repeatedly lace or otherwise secure a strap 3015 to the lever 45.

Figures 10A, 10B:
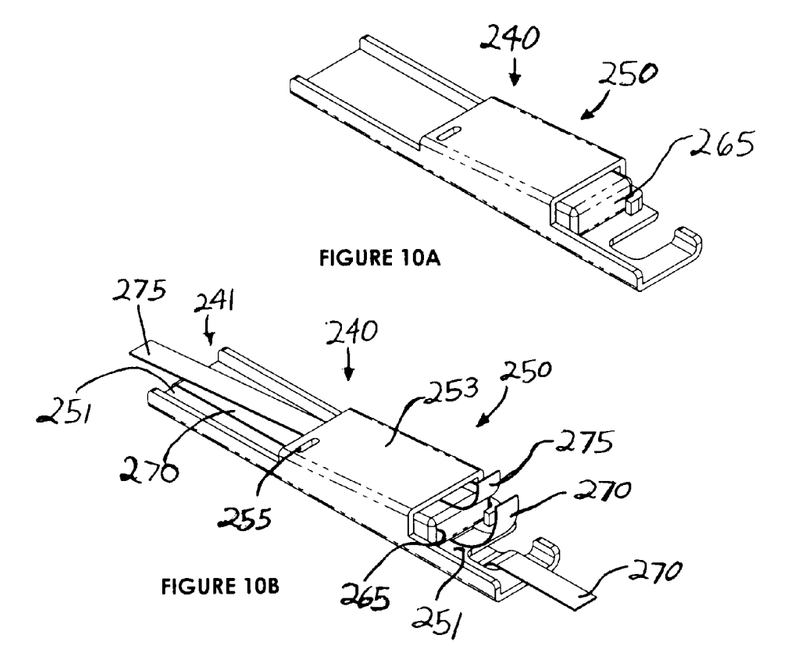
FIG. 10A is a top left isometric view of the lever of FIG. 8 assembled with the slidable block of FIG. 9A.
FIG. 10B is a top left isometric view of the assembly of FIG. 10A including straps retained to the lever of FIG. 8.
Figures 11, 12A, 12B:
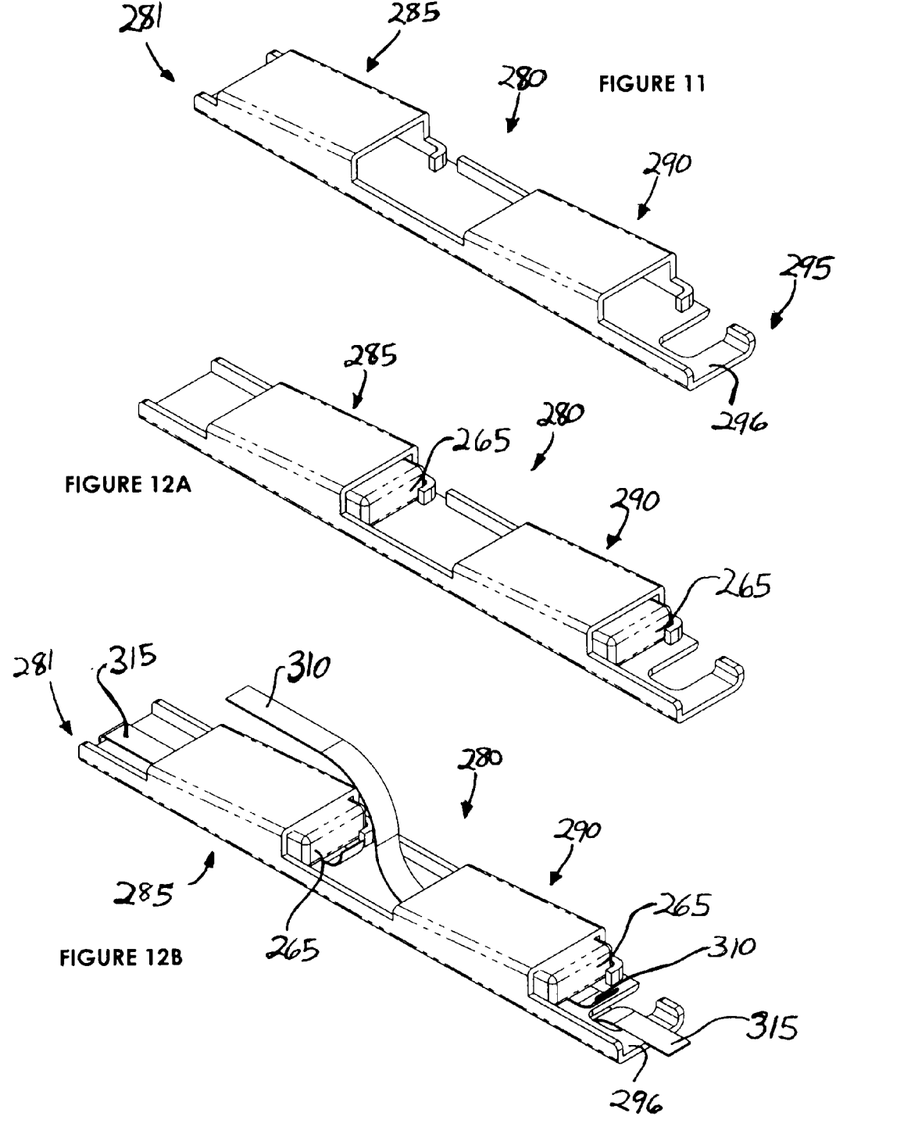
FIG. 11 is a top left isometric view of another lever for binding items.
FIG. 12A is a top left isometric view of the lever of FIG. 11 assembled with slidable blocks.
FIG. 12B is a top left isometric view of the assembly of FIG. 12A including straps retained to the lever of FIG. 11.
Figures 21A, 21B:
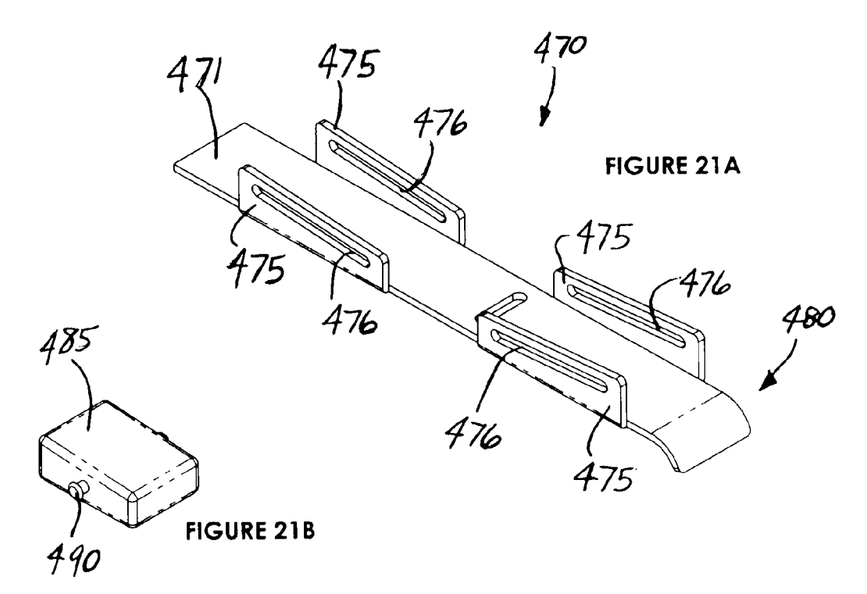
FIG. 21A is a top left isometric view of another lever for binding items.
FIG. 21B is a top left isometric view of a slidable block used with the lever of FIG. 21A.
Figure 21C:
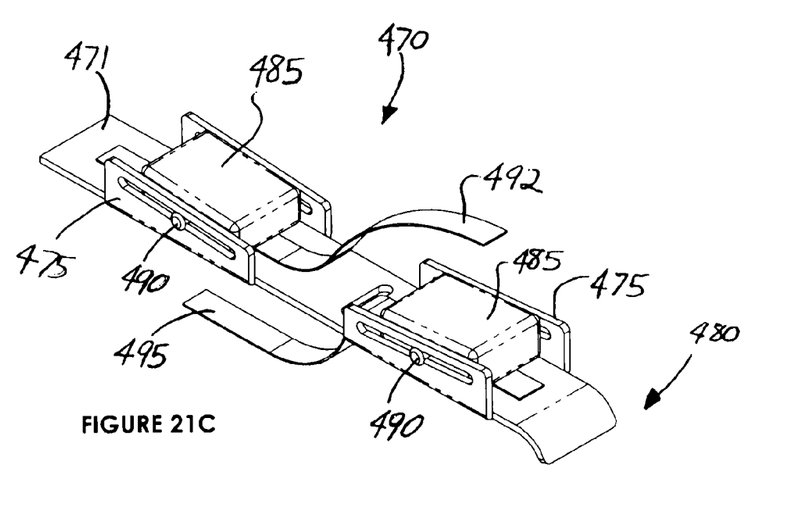
FIG. 21C is a top left isometric view of the lever of FIG. 21A assembled with two slidable blocks of FIG. 21B and with straps retained to the lever.

Other alternate arrangements for securing a second free end of a strap in a position where the second free end of a strap engages a lever distal from the axis end include those illustrated in FIGS. 10B (where strap 275 is illustrated engaging the lever 240 in the housing 250), 12B (where strap 310 is illustrated engaging the lever 280 in the housing 290), and FIG. 21C (where strap 492 is illustrated engaging lever 470 distal from the axis end 480).

Figures 8, 9A, 9B:
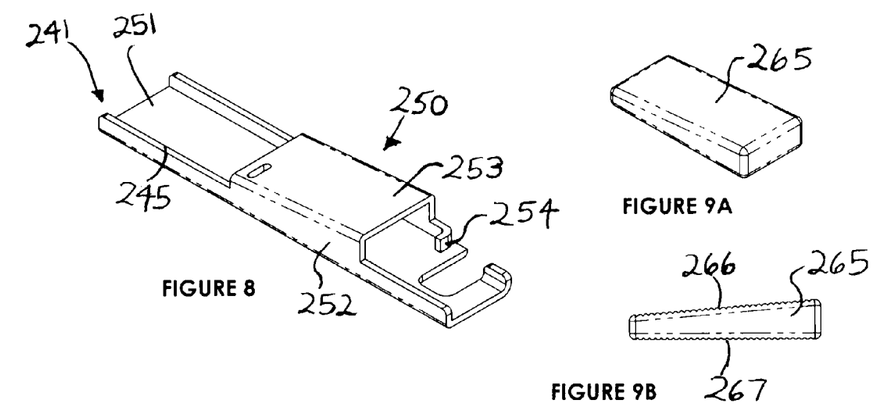
FIG. 8 is a top left isometric view of another lever for binding items.
FIG. 9A is a top left isometric view of a slidable block used with the lever of FIG. 8.
FIG. 9B is a left side view of the slidable block of FIG. 9A.

Alternate preferred strap retaining devices are illustrated in FIGS. 8-10B, 11-12B, and 21A-C. In FIG. 8, a lever 240 is illustrated with a housing 250. Housing 250 may include sidewalls 252, a roof 253, and a floor that includes the portion of the top surface 251 that underlies the roof 253. A slidable block 265 fits in the housing 250, and is preferably retained to the lever 240 by arm 254. The slidable block 265 may have a rough surface 266, 267 on the top and bottom of the block 265. A first free end of strap 270 may be placed between the slidable block 265 and the floor of the housing 250 when the slidable block is in a first position. Likewise, a second free end of strap 275 is placed between the slidable block 265 and the roof 253 of the housing 250 when the slidable block is in the first position. Sliding the block 265 to a second position secures the first free end of the strap 270 and the second free end of the strap 275 in positions where the first free end of the strap 270 is secured proximate the axis end 241 and the second free end of the strap 275 is secured distal from the axis end 241. Referring to FIG. 10B, a release mechanism 255 may be included. For example, the release mechanism 255 may include a slot through the roof 253 that permits an object to be inserted through the roof 253 to move the block 265 away from the axis end 241.

Figure 13:
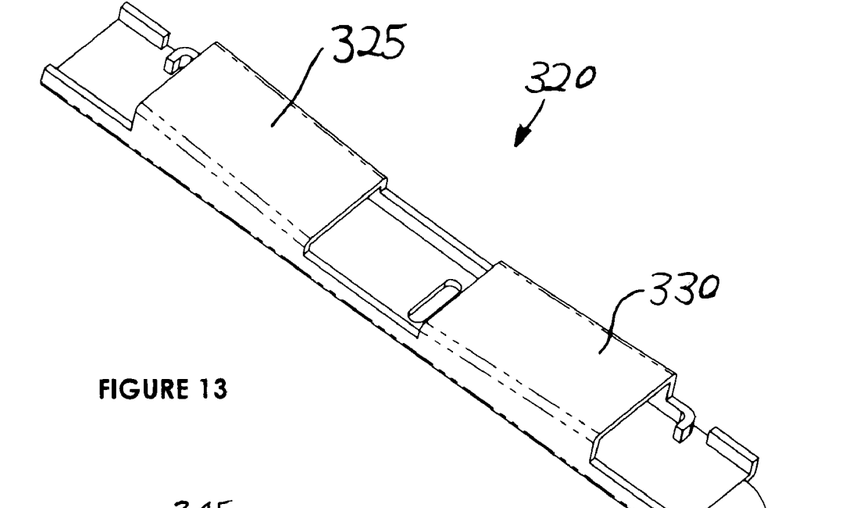
FIG. 13 is a top left isometric view of another lever for binding items.
Figure 14:
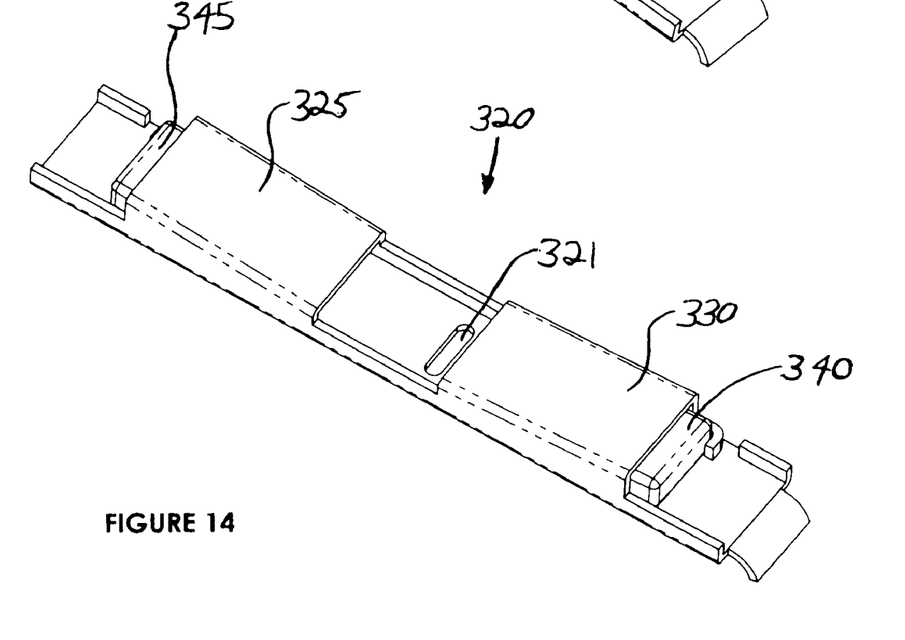
FIG. 14 is a top left isometric view of the lever of FIG. 13 assembled with slidable blocks.
Figures 15, 15A:
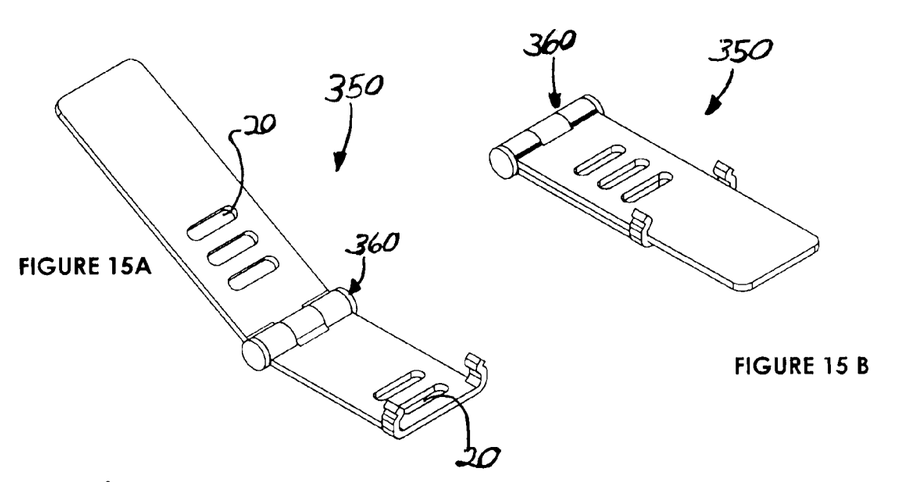
FIG. 15A is a top left isometric view of another lever for binding items in an open position.
Figure 16:
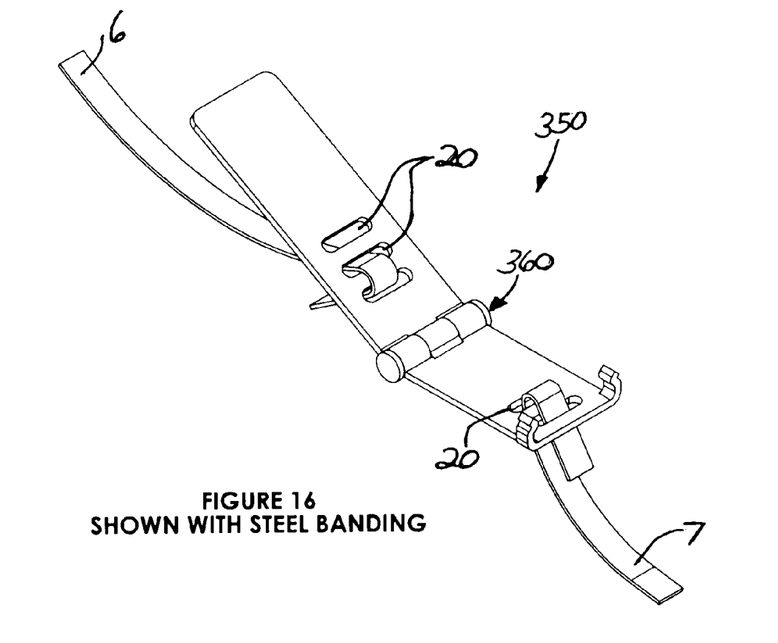
FIG. 16 is a top left isometric view of the lever of FIG. 15A with straps retained to the lever.
Figure 22:
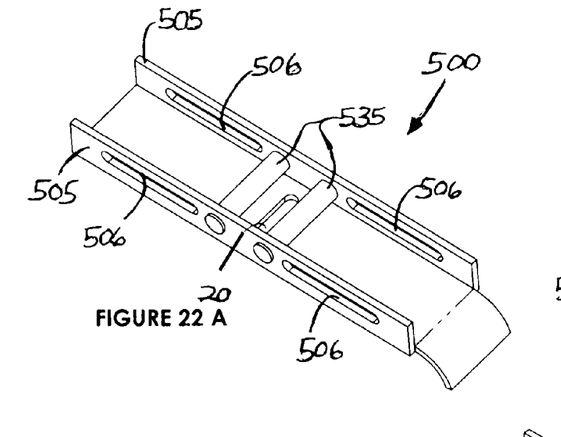
FIG. 22A is a top left isometric view of another lever for binding items.
FIG. 22B is a top left isometric view of a slidable block used with the lever of FIG. 22A.
FIG. 22C is a top left isometric view of the lever of FIG. 22A assembled with two slidable blocks of FIG. 22B.
FIG. 22D is a top left isometric view of another lever for binding items.
FIG. 22E is a top left isometric view of the lever of FIG. 22D with straps retained to the lever.

Alternatively, two housings 285, 290 (FIGS. 11-12B) may be used to secure the first free end of a strap 315 proximate the axis end 281 and to secure the second free end of a strap 310 distal from the axis end 281. For example, FIGS. 13-14 show another lever 320 with two housings 325, 330 and two blocks 340, 345 that are slidable toward a centrally located aperture 321. In FIGS. 21A-C, the housings include sidewalls 475 and the portion of the top surface 471 of the lever 470 that lies between the sidewalls 475. Slots 476 are preferably not parallel with the top surface 471. Sliding the blocks 485, that are retained in the slots 476 by pins 490, moves the blocks 485 between a first position where straps 490 and 495 may be inserted between the blocks 485 and the top surface 471 and a second position where the straps 490 and 495 are secured between the blocks 485 and the top surface 471. Other configurations, illustrated by lever 500 in FIGS. 22A-C and by lever 525 in 22D-E, may wrap straps 540, 545 around blocks 530 that have pins 522 to retain the blocks 530 in slots 506 of sidewalls 505. As shown in FIG. 22E, the blocks 530 slide to pinch the straps 540, 545 between the blocks 530 and pins 535 due to the force resulting from tensioning the straps 540, 545 when the lever 525 is rotated to a closed position. While the pins 535 are illustrated as being round, the pins 535 may include flat surfaces, or other shaped surfaces, and the surfaces may match the opposing surface of the block 530. Another alternate embodiment to secure a free end of a strap uses a cam or other locking mechanism to secure a strap to the lever. For example, referring to FIGS. 20A-20E, a cam device 700, 705 (or other configuration) may be retained between wings 711. The cam device 700, 705 is rotated to a first position to permit a strap 715 to be placed between the cam device 700, 705 and the upper surface 712 of the lever 710. The cam device 700, 705 is then rotated, preferably using an actuation portion 701, 706, to a second position to lock the strap 715 in place. Another strap 720 is folded around an endmost aperture.

Figure 5B:
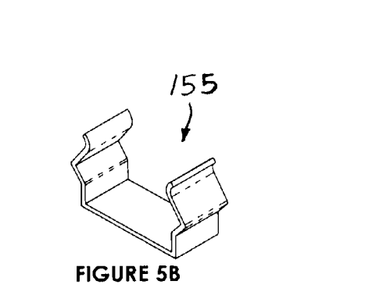
FIG. 5B is a top left isometric view of another retaining clip.

Referring to FIG. 1A, the lever 5 may also include a locking device. The lever 5 is illustrated with locking device 30, which includes a bent portion of the lever 5 near the axis end 15. The lever 5 is also illustrated with a locking aperture 35, which engages with a retaining clip, such as the retaining clip 155 illustrated in FIG. 5B, as described below.

FIG. 1B illustrates a protective boot 40 that may be placed over the axis end 15 of the lever 5 to protect the surface of an item to be bound by straps. The boot 40 is preferably made from a soft material such as rubber, nylon, wood, or other suitable material. A protective boot is a device or structure that operates to protect the item being bound from being marred by the lever, and may take other forms, such as plate 440 or 437, shown in FIGS. 18B and 19B, respectively.

Figure 18A:
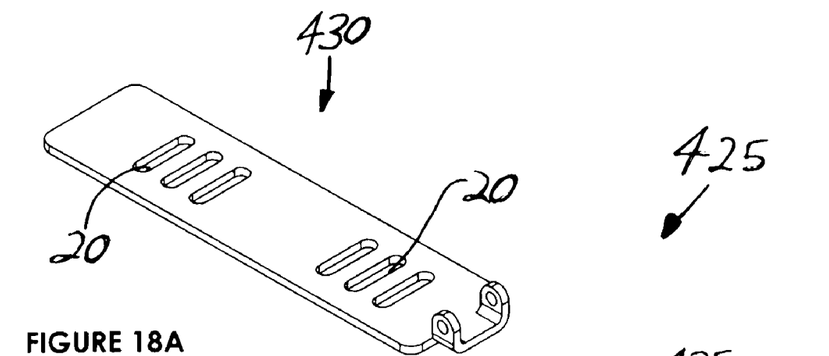
FIG. 18A is a top left isometric view of another lever for binding items.
Figure 18B:
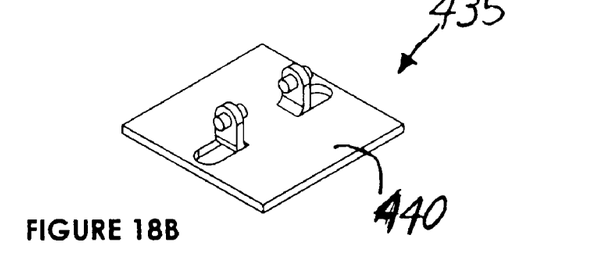
FIG. 18B is a top left isometric view of a base used with the lever of FIG. 18A.
Figure 18C:
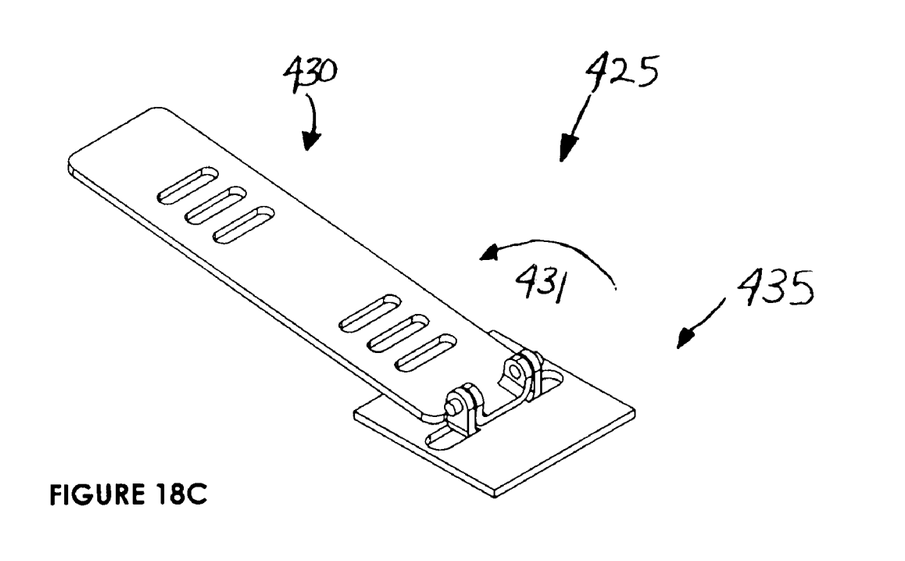
FIG. 18C is a top left isometric view of the lever of FIG. 18A assembled with the base of FIG. 18B.
Figure 19A:
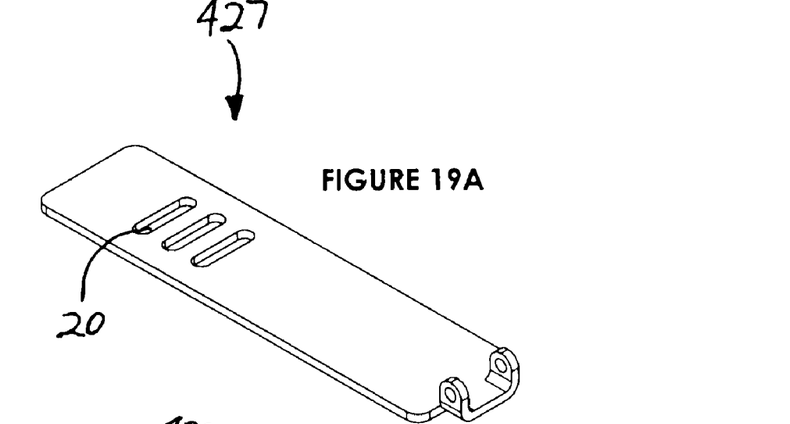
FIG. 19A is a top left isometric view of another lever for binding items.
Figure 19B:
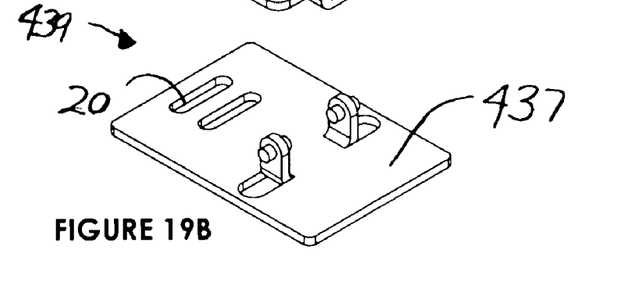
FIG. 19B is a top left isometric view of another base used with the lever of FIG. 19A.
Figure 19C:
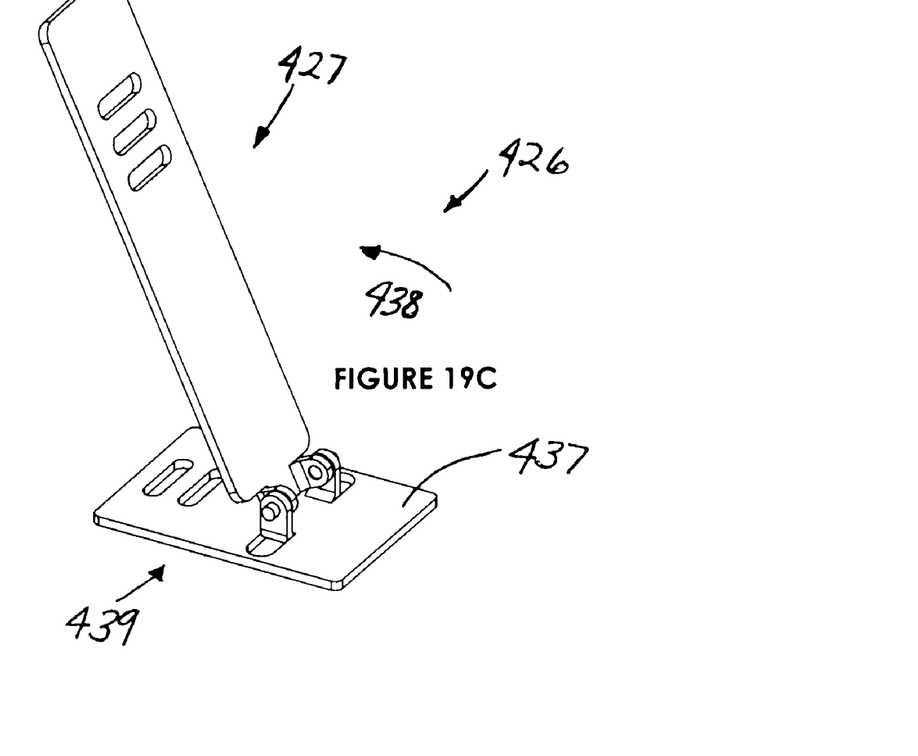
FIG. 19C is a top left isometric view of the lever of FIG. 19A assembled with the base of FIG. 19B.

Alternate embodiments may include a hinge 360, as illustrated by a lever 350 of FIGS. 15A-16, 18A-C, and 19A-C. When the hinge 360 is used, the axis of rotation may move from being proximate to an item being bound with the strap to a location above the item being bound with the strap, as illustrated in FIGS. 18C and 19C, for example. In FIGS. 18B and 19B, the plate assembly 435, and 439, respectively, may serve to protect an item from being marred when the lever 430 or 427, respectively, is rotated to a closed position. The device 425, 426 illustrated in FIGS. 18C and 19C, respectively, may therefore include an over-center locking device that operates by rotating the lever 430 or 427 in the direction of arrow 431 or 438, respectively, to a closed position.

Figure 17A:
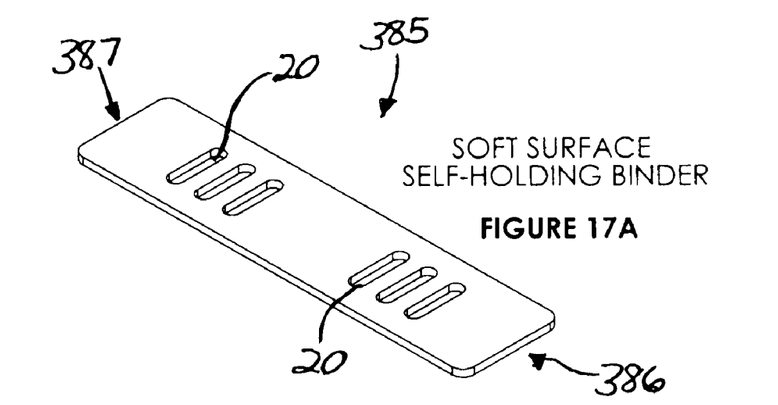
FIG. 17A is a top left isometric view of another lever for binding items.
Figure 17B:
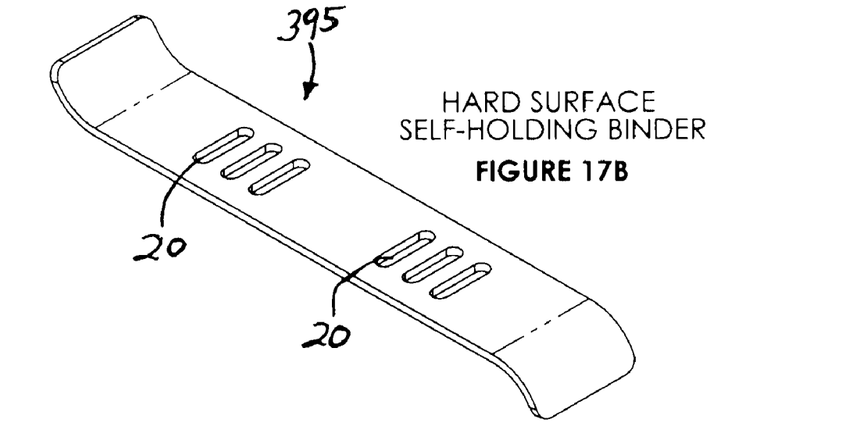
FIG. 17B is a top left isometric view of another lever for binding items.
Figure 17C:
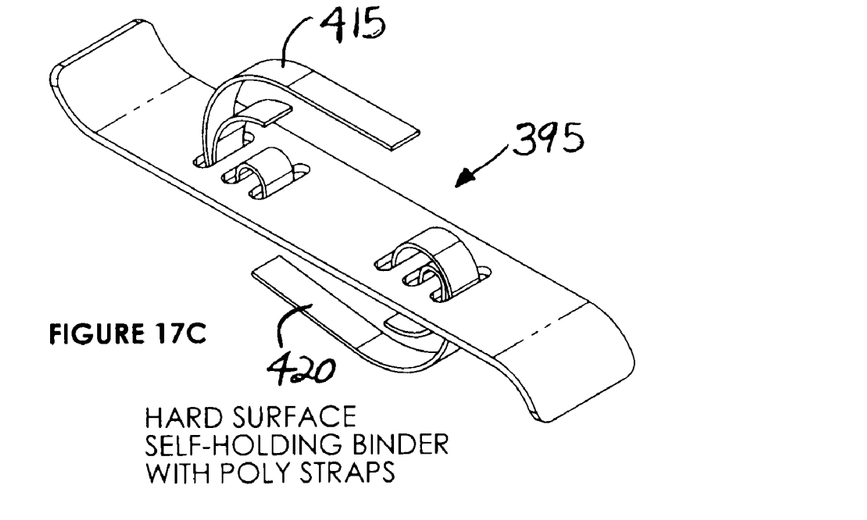
FIG. 17C is a top left isometric view of the lever of FIG. 17B with straps retained to the lever.

Another preferred configuration, illustrated in FIG. 17A, may use a flexible material for the lever 385, such as spring steel, nylon, high density polyethylene, or other suitable material, that may permit the lever 385 to flex. Such a configuration may use one end 386 as an axis end and end 387 as a distal end. When the lever 385 is rotated to a closed position, the axis end 386 may be maneuvered so that a portion of the axis end 386 underlies the strap secured distal from axis end 386. Placing the axis end 386 under the strap that is secured distal from the axis end 386 may lock the lever 385 in place. FIGS. 17B and 17C show another lever 395 for binding items, with straps 415, 420 shown retained to the lever 395 in FIG. 17C.

Figure 6:
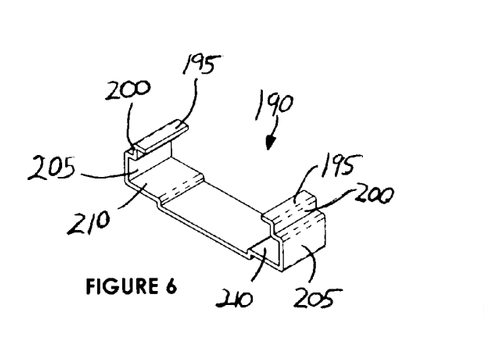
FIG. 6 is a top left isometric view of another retaining clip.
Figure 7:
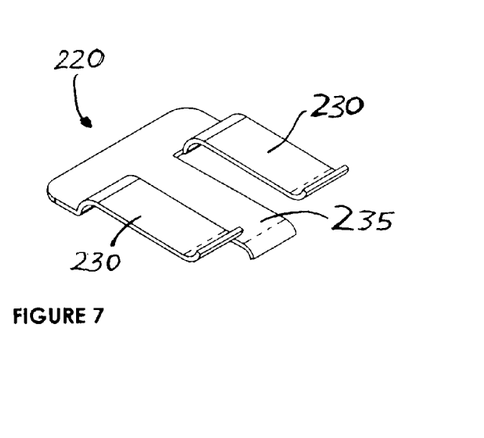
FIG. 7 is a top left isometric view of another retaining clip.

Another alternative may be to use a retaining clip 155 (FIG. 5B) that engages the lever 80 using the locking aperture 110 (FIG. 1D) instead of engaging the sides of the lever 80 as the retaining clip 140 does. An alternative retaining clip 190 may engage the sides of a lever in a manner where the retaining clip 190 is not readily released from the lever. Referring to FIG. 6, for example, the retaining clip 190 may include a release feature, such as a screwdriver slot defined by walls 200, 205, and 210, where a screwdriver may be used to pry wings 195 away from one another to release the retaining clip 190 from a lever. Readily engageable and releasable clips, such as those illustrated in FIGS. 5A, 5B, and 7, may or may not include a release feature. Referring to FIG. 7, for example, another alternative retaining clip 220 may engage a lever using arms 230 and 235. Arms 230 may contact one side of the lever when in the closed position and the arm 235 may contact the opposite side of the lever. A retaining clip such as the retaining clip 220 may be useful to lock a lever in a closed position when a lever does not contact an item, for example when the lever is suspended in the air because of the tension on the strap.

Figure 4A:
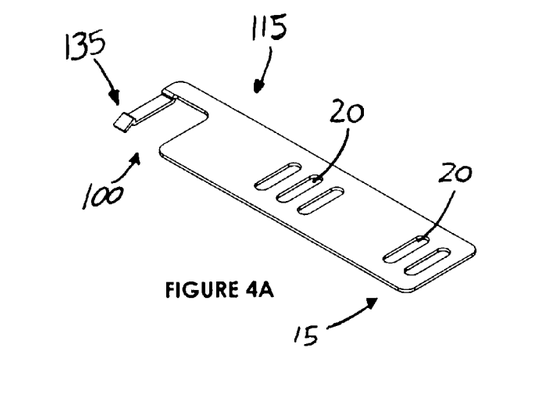
FIG. 4A is a top left isometric view of another lever for binding items.
Figure 4B:
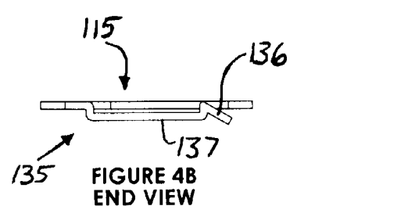
FIG. 4B is an end view of the lever of FIG. 4A.

Other preferred configurations include a locking device, such as the locking device 135 (FIG. 4A), that is configured as a strap engaging portion on the lever. For example, when the lever 115 is rotated to a closed position, the locking device 135 is maneuvered so that ramp portion 136 (FIG. 4B) engages a strap (not illustrated) and used to push the strap to rest in cradle 137. Another example is illustrated in FIG. 12B where strap 315 is resting in cradle 296 of locking device 295. Note that the locking device 295 does not include a ramp, but it may in alternative configurations.

It will be obvious to those having skill in the art that many changes may be made to the details of the above-described embodiments, including, but not limited to, mixing different types of locking devices and strap retaining features on a lever, without departing from the underlying principles of the invention. The scope of the present invention should, therefore, be determined only by the following claims.

The invention claimed is:

1. A method of using a multi-component clamp assembly to releasably secure a volumetric object to a retaining structure, the volumetric object having an outer surface and the clamp assembly including first and second non-extensible, flexible strap portions and a binder lever, the first strap portion having a first length and a first free end terminating in a first folded portion; the second strap portion having a second length and a second free end terminating in a second folded portion; and the binder lever having upper and lower surfaces, an axis end, a free end, and a lever length along which multiple apertures are mutually spaced apart, the method comprising:

engaging the first and second strap portions to the retaining structure and positioning the volumetric object between the first and second strap portions;

routing the first and second strap portions so that they and the retaining structure cooperate to encompass the outer surface of the volumetric object;

inserting the first folded portion through at least one of the apertures located in proximity to the axis end of the binder lever, and inserting the second folded portion through different ones of the apertures located in proximity to the free end of the binder lever, so that the first and second folded portions loop over different ones of the upper and lower surfaces of the binder lever; and rotating the binder lever about the axis end so that the binder lever lies against but is not coupled to the outer surface of the volumetric object, the distance between the first and second folded portions being selected to set a tension in the first and second strap portions to hold the outer surface of the volumetric object against the retaining structure and to hold the binder lever against the outer surface of the volumetric object.

2. The method of claim 1, further comprising:

passing the first free end through at least two consecutive apertures of the multiple apertures to form the first folded portion and thereby define a first binder lever region located in proximity to the axis end of the binder lever so that the first folded portion spans the first binder lever region; and passing the second free end through more than two consecutive apertures of the multiple apertures to form the second folded portion and thereby define a second binder lever region located in proximity to the free end of the binder lever so that the second folded portion spans the second binder lever region.

3. The method of claim 1, in which the volumetric object is a cylindrical tank.

4. The method of claim 3, in which the binder lever is curved along its lever length.

5. The method of claim 1, in which the first and second strap portions are separate, discrete component parts.

6. The method of claim 5, in which the first and second strap portions have respective first and second attachment ends, and in which the engaging the first and second strap portions includes fastening the first and second attachment ends to the retaining structure.

7. The method of claim 1, further comprising locking in a fixed position the binder lever lying against the outer surface of the volumetric object.

8. The method of claim 7, further comprising positioning a retaining clip between the outer surface of the volumetric object and the second strap portion to receive the free end of the binder lever.

9. The method of claim 1, in which the binder lever includes longer and shorter hinge portions connected by a hinge, and in which the rotating of the binder lever includes rotating the longer hinge portion about the hinge.

10. The method of claim 9, further comprising operatively connecting a retaining clip to the shorter hinge portion to receive the longer hinge portion when it is rotated about the hinge to lock the binder lever in a fixed position.

11. The method of claim 1, in which the binder lever is curved along its lever length.

* * * * *